United States Patent
Hughes et al.

(10) Patent No.: US 12,165,758 B1
(45) Date of Patent: *Dec. 10, 2024

(54) CLOUD-ASSISTED REHABILITATION METHODS AND SYSTEMS FOR MUSCULOSKELETAL CONDITIONS

(71) Applicant: CARKMH, LLC, Springfield, OR (US)

(72) Inventors: Rexford Irving Hughes, Springfield, OR (US); Daniel Charles Fitzpatrick, Eugene, OR (US); Cale Gage Bruckner, Eugene, OR (US); Howard Wayne Skipper, Eugene, OR (US)

(73) Assignee: CARKMH, LLC, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/336,445

(22) Filed: Jun. 16, 2023

Related U.S. Application Data

(60) Continuation of application No. 17/681,763, filed on Feb. 26, 2022, now Pat. No. 11,721,424, which is a
(Continued)

(51) Int. Cl.
*G16H 20/30* (2018.01)
*A61B 5/00* (2006.01)
(Continued)

(52) U.S. Cl.
CPC ......... *G16H 20/30* (2018.01); *G09B 19/0038* (2013.01); *G16H 10/60* (2018.01);
(Continued)

(58) Field of Classification Search
CPC ........ G16H 20/30; G16H 10/60; G16H 20/40; G16H 40/63; G16H 40/67; G09B 19/0038;
(Continued)

(56) References Cited

U.S. PATENT DOCUMENTS

2008/0275309 A1* 11/2008 Stivoric ............... G16H 10/60
600/300
2009/0069642 A1* 3/2009 Gao ..................... H04L 67/125
600/300
(Continued)

FOREIGN PATENT DOCUMENTS

WO WO-2013072234 A1 * 5/2013 ........... A61B 5/0022

OTHER PUBLICATIONS

Helmer et al., Wild Monitoring: Linking Performance, Physiology and Biomechanics Live, ISBS-Conference Proceedings Archive, vol. 1, No. 1, 2012 (Year: 2012).*
(Continued)

*Primary Examiner* — Joy Chng
(74) *Attorney, Agent, or Firm* — Renaissance IP Law Group, LLP; David A. Crowther

(57) ABSTRACT

Embodiments of the invention include a cloud-assisted rehabilitation system for assisting in the rehabilitation of musculoskeletal conditions, and a method for rehabilitating patients having musculoskeletal conditions. A rehabilitation portal can aggregate and de-identified musculoskeletal rehabilitation information that is gathered from various intelligent musculoskeletal rehabilitation apparatuses attached to a group of patients. The rehabilitation portal can facilitate crowd communication among the group of patients. A particular rehabilitation experience can be compared with other rehabilitation experiences and data from other patients. The rehabilitation portal can also facilitate crowd communication among a group of healthcare professionals so that the plurality of healthcare professionals can communicate with each other and compare information regarding different rehabilitation experiences based at least on the aggregated de-identified musculoskeletal rehabilitation information.

20 Claims, 12 Drawing Sheets

Related U.S. Application Data division of application No. 16/245,887, filed on Jan. 11, 2019, now Pat. No. 11,289,184, which is a continuation of application No. 14/687,552, filed on Apr. 15, 2015, now Pat. No. 10,216,904.

(60) Provisional application No. 61/980,048, filed on Apr. 16, 2014.

(51) Int. Cl.

| | | |
|---|---|---|
| *A61B 5/107* | (2006.01) | |
| *A61B 5/11* | (2006.01) | |
| *A61H 1/02* | (2006.01) | |
| *G09B 19/00* | (2006.01) | |
| *G16H 10/60* | (2018.01) | |
| *G16H 20/40* | (2018.01) | |
| *G16H 40/63* | (2018.01) | |
| *G16H 40/67* | (2018.01) | |

(52) U.S. Cl.
CPC ............ *G16H 20/40* (2018.01); *G16H 40/63* (2018.01); *G16H 40/67* (2018.01); *A61B 5/002* (2013.01); *A61B 5/1073* (2013.01); *A61B 5/112* (2013.01); *A61B 5/1121* (2013.01); *A61B 5/4585* (2013.01); *A61B 5/6831* (2013.01); *A61B 2505/09* (2013.01); *A61H 1/0237* (2013.01); *A61H 1/024* (2013.01); *A61H 2201/164* (2013.01); *A61H 2201/165* (2013.01); *A61H 2201/501* (2013.01); *A61H 2201/5043* (2013.01); *A61H 2201/5048* (2013.01); *A61H 2201/5084* (2013.01)

(58) Field of Classification Search
CPC ....... A61B 5/002; A61B 5/1073; A61B 5/112; A61B 5/1121; A61B 5/4585; A61B 5/6831; A61B 2505/09; A61H 1/0237; A61H 1/024; A61H 2201/164; A61H 2201/165; A61H 2201/501; A61H 2201/5043; A61H 2201/5048; A61H 2201/5084
USPC ......................................................... 705/2–3
See application file for complete search history.

(56) References Cited

U.S. PATENT DOCUMENTS

| | | | | |
|---|---|---|---|---|
| 2012/0278095 | A1* | 11/2012 | Homchowdhury | .... G16H 80/00 705/2 |
| 2014/0257141 | A1* | 9/2014 | Giuffrida | ............. A61B 5/1124 600/595 |

OTHER PUBLICATIONS

Nanayakkara et al., Development of a wearable remote health conditions monitoring system, Aug. 18, 2013, Industrial and Information Systems (ICIIS), 2013 8th IEEE International Conference on Digital Object Identifier: 10.1109/ICIInfS.2013.6731967, pp. 122-127 (Year: 2013).*

Ruiz-Zafra, et al., Mobile cloud-supported e-rehabilitation platform for brain-injured patients, May 5-8, 2013, pp. 352-355, E-ISBN: 978-1-936968-80-0, Print ISBN: 978-1-4799-0296-5, INSPEC Accession No. 13679697 (Year: 2013).*

* cited by examiner

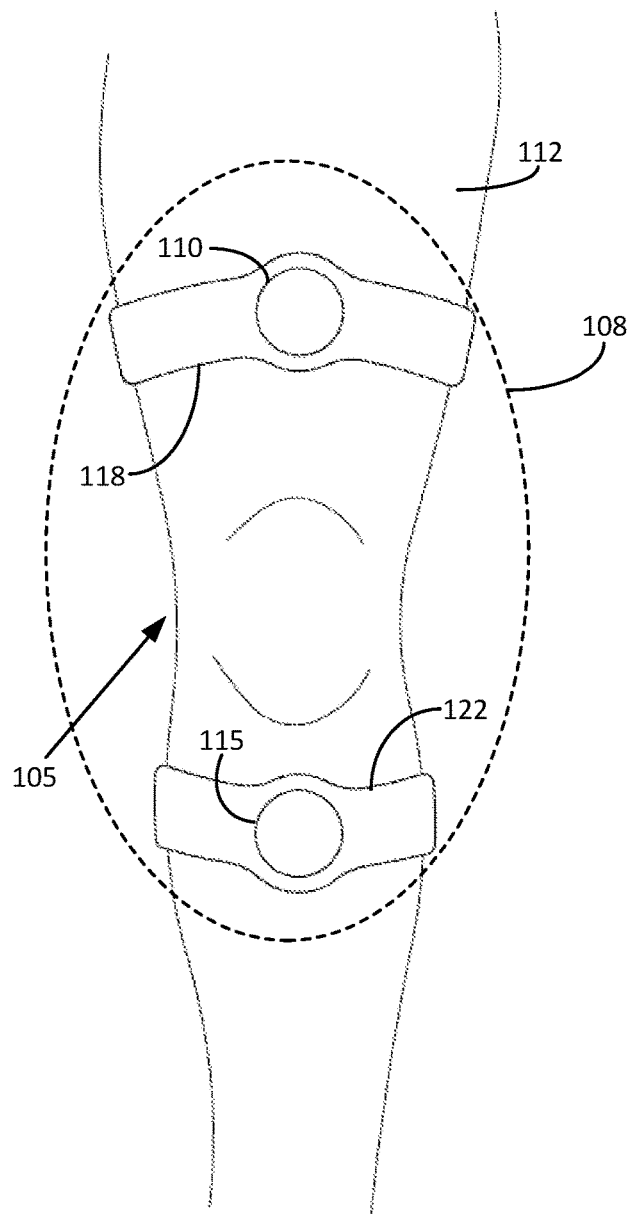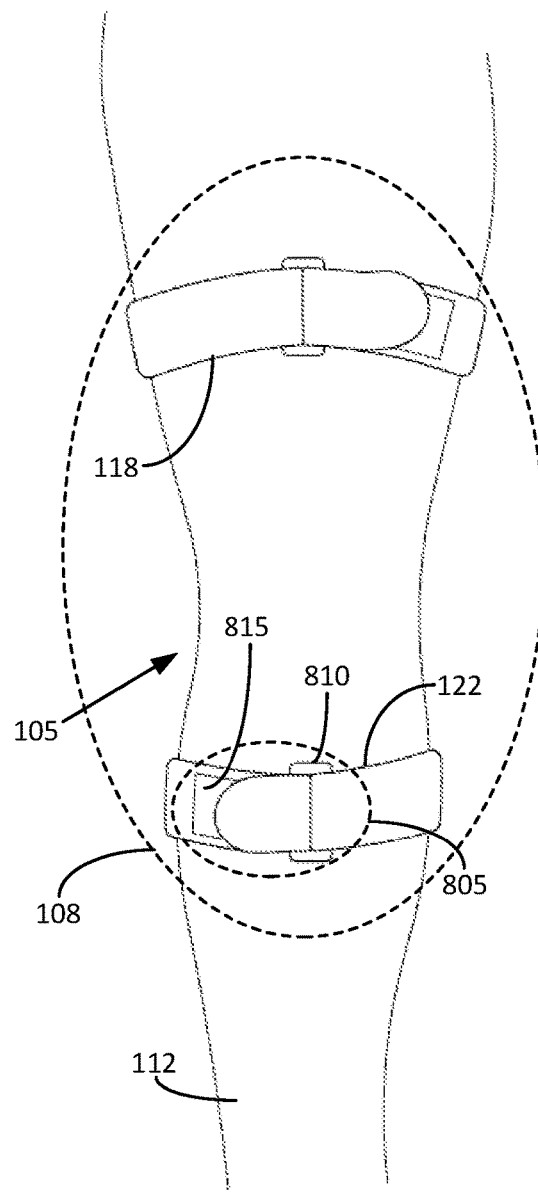
FIG. 8B
FIG. 8C

CLOUD-ASSISTED REHABILITATION METHODS AND SYSTEMS FOR MUSCULOSKELETAL CONDITIONS

RELATED APPLICATION DATA

This application is a continuation of U.S. application Ser. No. 17/681,763, filed on Feb. 26, 2022, which is a divisional of U.S. application Ser. No. 16/245,887, filed on Jan. 11, 2019, now U.S. Pat. No. 11,289,184, which is a continuation of U.S. application Ser. No. 14/687,552, filed on Apr. 15, 2015, now U.S. Pat. No. 10,216,904, which claims the benefit of U.S. provisional Application Ser. No. 61/980,048, filed Apr. 16, 2014, which are hereby incorporated by reference.

FIELD OF THE INVENTION

This application pertains to cloud-assisted rehabilitation methods and systems, and more particularly, to cloud-assisted rehabilitation methods and systems for treatment of musculoskeletal conditions, injuries, and/or preoperative and postoperative human musculoskeletal surgeries.

BACKGROUND

Preparation for and recovery from injury or surgery on the musculoskeletal system, such as a knee, elbow, wrist, and the like, can be a long and painstaking experience. Likewise, recovery from a host of non-surgical musculoskeletal conditions often requires prolonged exercises for recovery of range of motion and strength. Traditional rehabilitation requires a multitude of visits to a physician and therapy office. Very little interaction occurs between the patient and the healthcare provider between visits. The healthcare provider has little direct insight into the status of the patient for much of the recovery process. It is difficult to share and compare recovery information and statistics between healthcare professionals using conventional physical therapy techniques.

For example physical therapy for knee conditions can be especially intensive and require particular attention by medical professionals. Patellar Chondromalacia-a form of cartilage damage-requires prolonged exercises for strengthening of the extensors to allow return to function. For total knee arthroplasty (i.e., total knee replacement), these patients typically range in age from 55-90 years old. They often need both preoperative and postoperative therapy. Anterior cruciate ligament (ACL) reconstruction patients typically range in age from 15-55 years old. They also require both preoperative and postoperative therapy. Knee arthroscopy patients typically range in age from 18-70 years old. These patients may benefit from postoperative physical therapy. Conventional preoperative and postoperative procedures and techniques are expensive and time consuming, leading to high overall costs due to an increased number of in-person visits, miscommunications, patients' failures to follow recommended recovery guidelines, and the like.

Accordingly, a need remains for improved methods and systems for assisting patients and providers with rehabilitation associated with musculoskeletal conditions. Embodiments of the invention address these and other limitations in the prior art.

BRIEF DESCRIPTION OF THE DRAWINGS

FIGS. 8A-8C illustrate example embodiments of an intelligent musculoskeletal rehabilitation apparatus according to some embodiments of the present invention.

The foregoing and other features of the invention will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first wireless network connection could be termed a second wireless network connection, and, similarly, a second wireless network connection could be termed a first wireless network connection, without departing from the scope of the inventive concept.

It will be understood that when an element or layer is referred to as being "on," "coupled to" or "connected to" another element or layer, it can be directly on, directly coupled to or directly connected to the other element or layer, or intervening elements or layers may be present. In contrast, when an element is referred to as being "directly on," "directly coupled to" or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
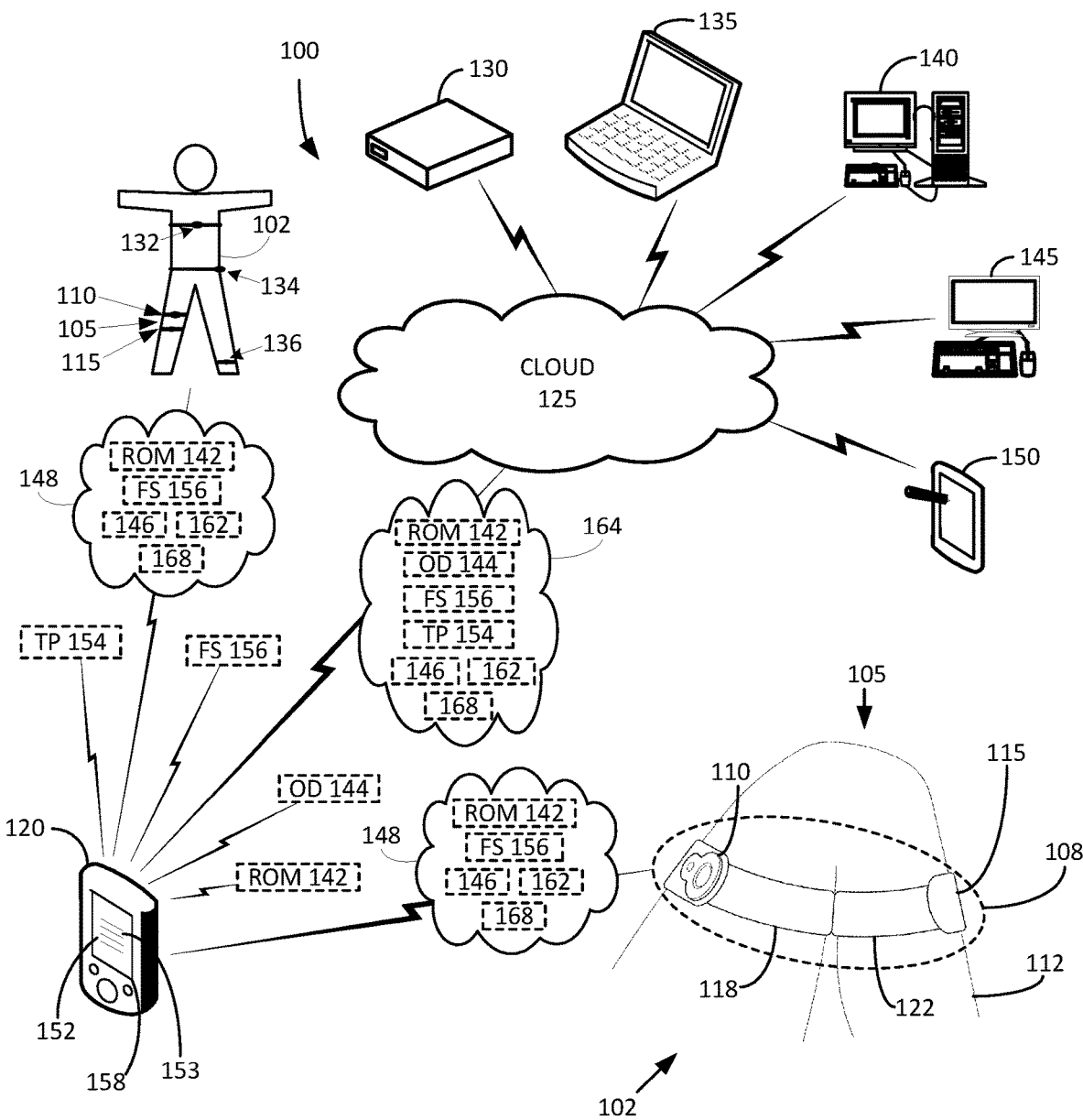
FIG. 1 illustrates a diagram of an example cloud-assisted system for musculoskeletal rehabilitation in accordance with various embodiments of the present invention.

FIG. 1 illustrates a diagram of an example cloud-assisted rehabilitation system 100 for rehabilitation of musculoskeletal conditions in accordance with various embodiments of the present invention. An intelligent musculoskeletal rehabilitation apparatus 108 can include straps (e.g., 118 and 122) for wrapping around one or more human limbs (e.g., 112) that are proximately located to a human joint, such as a knee 105. The intelligent musculoskeletal rehabilitation apparatus 108 can include a hinged brace, for example, in which the straps 118 and 122 are connected to the hinged brace as further described below, which can provide additional support for the human joint 105. The intelligent musculoskeletal rehabilitation apparatus 108 can include an internal or external attachment for attaching to the one or more human limbs 112 and/or to the joint 105. The intelligent musculoskeletal rehabilitation apparatus 108 can include one or more intelligent rehabilitation members (e.g., 110, 115, 132, 134, and/or 136) to measure range-of-motion (ROM) data 142 for an entire extremity and/or for one or more limbs of a human patient 102. Alternatively or in addition, the one or more intelligent rehabilitation members (e.g., 110, 115, 132, 134, and/or 136) can measure musculoskeletal conditions data 146 including temperature, limb circumference (swelling), gait patterns, step counts, or the like.

For example, the intelligent musculoskeletal rehabilitation apparatus 108 can include a first intelligent rehabilitation member 110 and/or a second intelligent rehabilitation member 115. Alternatively or in addition, the intelligent musculoskeletal rehabilitation apparatus 108 can include multiple intelligent rehabilitation members (e.g., 110, 115, 132, 134, and/or 136) that can be attached to various parts or locations of the patient 102. For example, the intelligent musculoskeletal rehabilitation apparatus 108 can include an intelligent rehabilitation member 132 that can be attached to the back of the patient 102. By way of another example, the intelligent musculoskeletal rehabilitation apparatus 108 can include an intelligent rehabilitation member 134 that can be attached to a hip of the patient 102. By way of yet another example, the intelligent musculoskeletal rehabilitation apparatus 108 can include an intelligent rehabilitation member 136 that can be attached to an ankle of the patient 102. It will be understood that the one or more intelligent rehabilitation members can be attached to a neck, a head, a hand, a chest, a torso, a foot, or other suitable location, of the patient 102.

Alternatively, the intelligent musculoskeletal rehabilitation apparatus 108 can include a single intelligent rehabilitation member, for example, selected from among the rehabilitation members 110, 115, 132, 134, and/or 136, or the like.

The intelligent musculoskeletal rehabilitation apparatus 108 can transmit musculoskeletal rehabilitation information 148 in real-time, and/or periodically, by the one or more intelligent rehabilitation members (e.g., 110, 115, 132, 134, and/or 136), to a mobile device such as smart phone 120, over a short-range wireless connection such as Bluetooth®. The musculoskeletal rehabilitation information 148 that is transmitted can include the musculoskeletal conditions data 146, which can include temperature, limb circumference (swelling), gait patterns, step counts, or the like. The musculoskeletal rehabilitation information 148 that is transmitted can include the ROM data 142. The ROM data 142 can be automatically gathered by the intelligent musculoskeletal rehabilitation apparatus 108. Alternatively or in addition, the ROM data 142 can be gathered through fillable forms 152 presented on a display 158 of the mobile device 120, which can be manually filled by the patient 102 or another person (not shown) who assists the patient 102. The mobile device 120 can save and/or transmit the ROM data 142, whether received from the one or more intelligent rehabilitation members (e.g., 110, 115, 132, 134, and/or 136) and/or through the fillable forms 152, as further described below.

Outcomes data 144 can be collected by the mobile device 120 using outcomes analytical tools, such as Western Ontario and McMaster Universities Arthritis Index (WOMAC), Short Form 36 (SF-36), Hospital for Special Surgery (HSS) Knee score, or the like. The outcomes data 144 can be collected by prompting the patient 102 fill out a questionnaire, survey, or form 152 at different times in the postoperative period. The mobile device 120 can receive, store, and/or transmit the outcomes data 144.

Alternatively or in addition, one or more functional scores 156 can be generated and/or collected at specified times postoperatively. The functional scores 156 can include, for example, a "get up and go" test, a walking test, or the like. The functional scores 156 can be automatically generated and/or collected by the intelligent musculoskeletal rehabilitation apparatus 108, and transmitted to the mobile device 120. Alternatively or in addition, the functional scores 156 can be generated based at least on information received manually from the patient 102.

Alternatively or in addition, total pain level 154 can be measured, for example, using a visual analog pain scale 153 presented on the display 158 of the mobile device 120. The mobile device 120 can receive input from the patient 102 regarding the patient's total pain level 154. The visual analog pain scale 153 can visually represent the total pain level 154.

Alternatively or in addition, a total level of function 162 can be collected. For example, the number of steps taken per day, the number of a particular repetitive motion, or other quantifiable information that provides insights into the total level of function 162 of the patient 102 can be automatically measured by the intelligent musculoskeletal rehabilitation apparatus 108, and transmitted to the mobile device 120.

Alternatively or in addition, exercise data 168 can be collected. For example, a number of exercise routines completed, a number of movement repetitions, the duration of certain exercises, or other quantifiable information that provides insights into the amount and kind of exercise performed by the patient 102 can be automatically measured by the intelligent musculoskeletal rehabilitation apparatus 108, and transmitted to the mobile device 120.

The mobile device 120 can aggregate and/or store the ROM data 142, the outcomes data 144, the one or more functional scores 156, the total pain level 154, the musculoskeletal conditions data 146, the total level of function 162, and/or the exercise data 168. The mobile device 120 can transmit aggregated musculoskeletal rehabilitation information 164 via the cloud 125 to a remote server 130. The aggregated musculoskeletal rehabilitation information 164 can include the ROM data 142, the outcomes data 144, the one or more functional scores 156, the total pain level 154, the musculoskeletal conditions data 146, the total level of function 162, and/or the exercise data 168, or the like.

Alternatively or in addition, the mobile device 120 can transmit the aggregated musculoskeletal rehabilitation information 164 via the cloud 125 to a variety of other devices such as a laptop computer 135, a desktop computer 140, a terminal 145, a smart tablet 150, or the like. Similarly, the mobile device 120 can receive feedback or other information from the remote server 130 and/or the other devices, as further described below.

Figure 2:
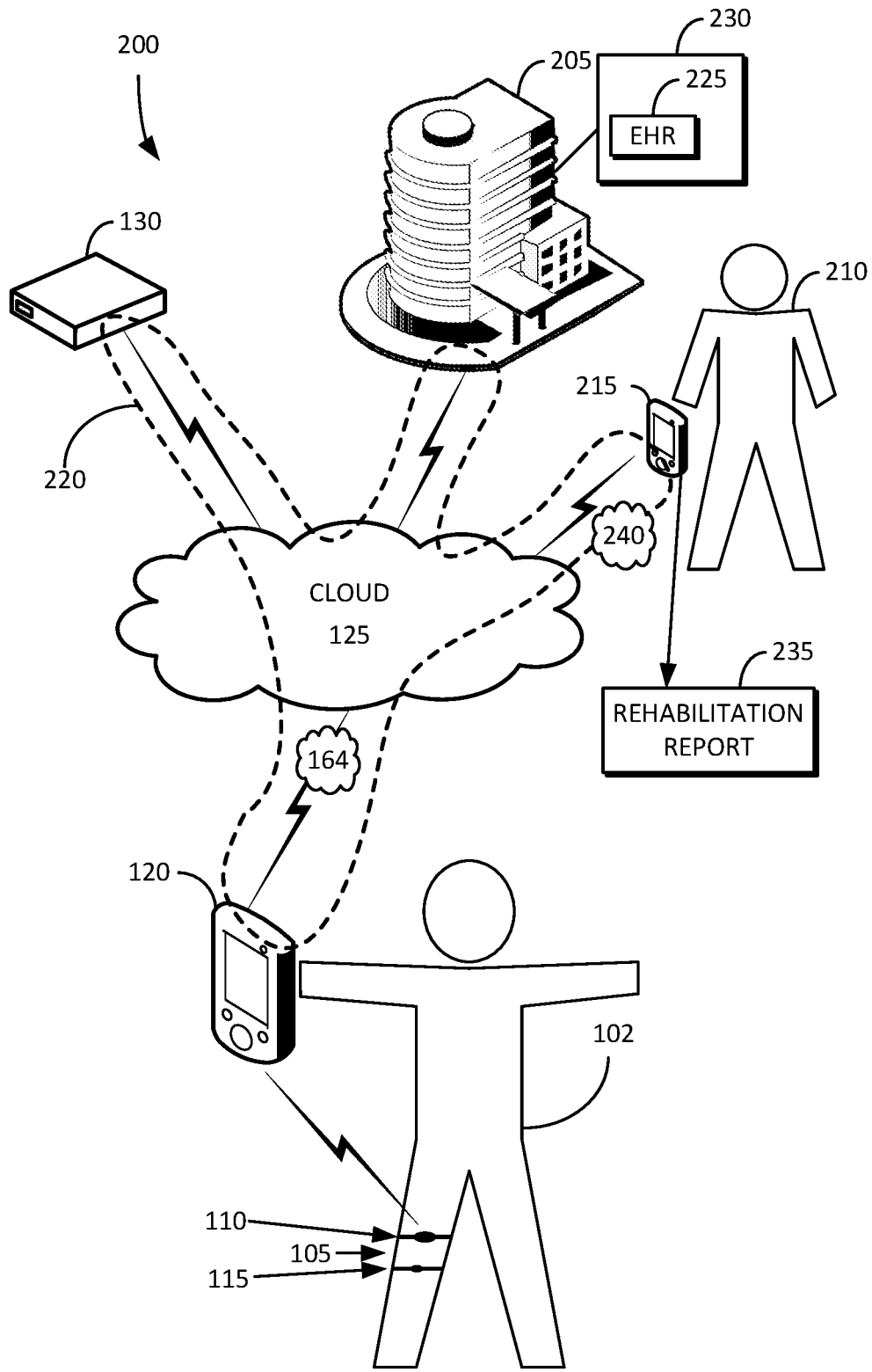
FIG. 2 illustrates another diagram of an example cloud-assisted system for musculoskeletal rehabilitation in accordance with various embodiments of the present invention.

FIG. 2 illustrates another diagram of an example cloud-assisted system 200 for rehabilitation of musculoskeletal in accordance with various embodiments of the present invention. The aggregated musculoskeletal rehabilitation information 164 can be uploaded to a rehabilitation portal 220 that allows one or more healthcare providers 210 (e.g., surgeon, physician, nurse, therapist, or the like) to view progress by reviewing the aggregated musculoskeletal rehabilitation information 164. For example, the aggregated musculoskeletal rehabilitation information 164 can be transmitted from the intelligent musculoskeletal rehabilitation apparatus 108 to the mobile device 120, and made accessible to the healthcare provider(s) 210 via the rehabilitation portal 220. Alternatively or in addition, the one or more healthcare providers 210 can track individual progress for a particular patient 102 over the course of the patient's rehabilitation via the rehabilitation portal 220. The rehabilitation portal 220 can include a client-side application and/or a server-side application, as further described below.

The mobile device 120 can include in part or otherwise be associated with the rehabilitation portal 220. In addition, a remote mobile device 215 can be carried by or otherwise accessible by the healthcare provider 210, and can also include in part or otherwise be associated with the rehabilitation portal 220. For example, the mobile device 120 and/or the remote mobile device 215 can have an application installed thereon, which allows the patient 102 and/or the healthcare provider(s) 210 to review the aggregated musculoskeletal rehabilitation information 164 via the rehabilitation portal 220. The rehabilitation portal 220 can include logic, hardware, a network, software, firmware, and/or a display, or the like, or any combination thereof. Alternatively or in addition, the aggregated musculoskeletal rehabilitation information 164 can be stored on the remote server 130 and/or transmitted to a healthcare provider office 205. The remote server 130 can include in part or otherwise be associated with the rehabilitation portal 220. Moreover, the healthcare provider office 205 can include one or more servers (e.g., such as 130) and/or one or more mobile devices (e.g., such as 215) that include in part or that are otherwise associated with the rehabilitation portal 220.

The rehabilitation portal 220 can alert the one or more healthcare providers 210 if the patient 102 is outside of predetermined goals for a specific point in time, allowing the one or more healthcare providers 210 to intervene with adjustments to an exercise program and/or recommend an earlier follow-up visit. The rehabilitation portal 220 can allow the aggregated musculoskeletal rehabilitation information 164 to be exported and/or uploaded to the healthcare provider's electronic health record (EHR) 225 for a given patient 102. The rehabilitation portal 220 can connect to or otherwise communicate with an EHR database 230 maintained or operated by the healthcare provider 210. The rehabilitation portal 220 can de-identify and report results on multiple patients based on specific patient characteristics, surgeon characteristics, injury characteristics, surgery characteristics, or the like, as further described below.

The rehabilitation portal 220 can allow the healthcare provider 210 to generate one or more rehabilitation reports 235 for outcomes studies. Moreover, the rehabilitation portal 220 can uniquely identify the patient 102. In some embodiments, the rehabilitation portal 220 can uniquely identify the patient 102 using non-personal-identifying information. The communication between the patient 102 and the healthcare provider 210 can comply with Health Insurance Portability and Accountability Act (HIPAA) requirements. The healthcare provider 210 can send feedback 240 back to the patient 102 for adjustment of exercises and/or to provide coaching and encouragement.

Figure 3:
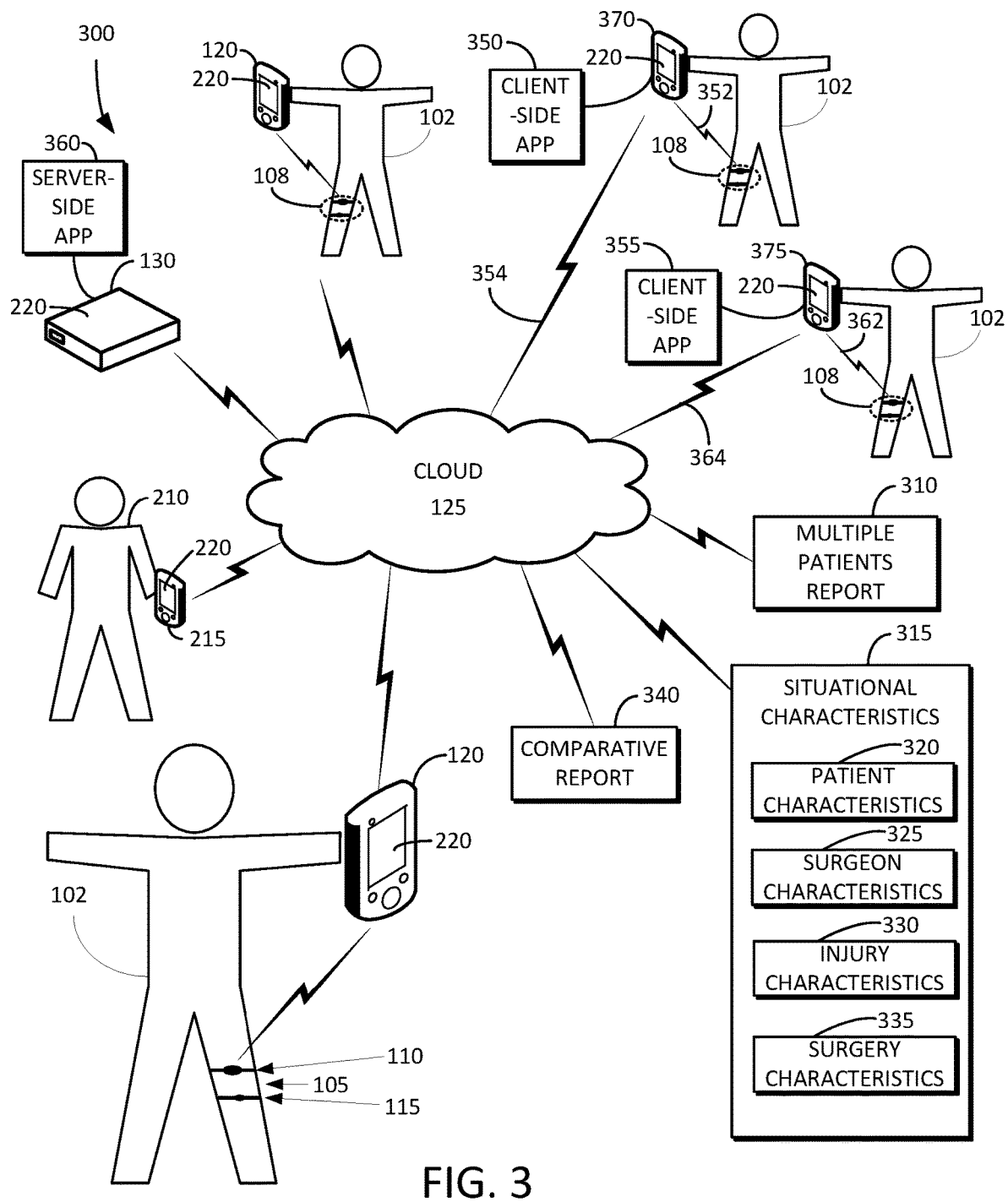
FIG. 3 illustrates yet another diagram of an example cloud-assisted system for musculoskeletal rehabilitation in accordance with various embodiments of the present invention.

FIG. 3 illustrates yet another diagram of an example cloud-assisted system 300 for musculoskeletal rehabilitation in accordance with various embodiments of the present invention. The rehabilitation portal 220 can collect and de-identify results on multiple patients 102. In other words, information that personally identifies the patients 102, for example, by name or other personally or sensitive identifying information, can be removed or otherwise hidden from view. It will be understood that while four patients 102 are shown, any suitable number of patients 102 can connect to the rehabilitation portal 220. The rehabilitation portal 220 can generate one or more multiple-patients reports 310 that are associated with the multiple patients 102 based at least on specific situational characteristics 315.

The situational characteristics 315 can include patient characteristics 320, surgeon characteristics 325, injury characteristics 330, surgery characteristics 335, or the like. The situational characteristics 315 can be automatically gathered from the various intelligent musculoskeletal rehabilitation apparatuses 108 associated with the various patients 102. Alternatively or in addition, the situational characteristics 315 can be automatically gathered from the EHR database 230 (of FIG. 2). The rehabilitation portal 220 can gather, store, and/or provide the one or more multiple-patients reports 310 based at least on the situational characteristics 315.

Healthcare providers (e.g., 210) can view the one or more multiple-patients reports 310 to evaluate techniques and make decisions about patient care. The multiple patients 102 can view the one or more multiple-patients reports 310 to compare their progress to that of a group of patients with similar characteristics.

The rehabilitation portal 220 allows the patient 102 to see how their data on a given postoperative day compares with that of all historical patients 102 who have had a similar surgery. Such information can be included in a comparative report 340. The comparative report 340 can be accessed by the patient 102 using the rehabilitation portal 220. Alternatively or in addition, the comparative report 340 can be pushed to the patient 102, for example, in an email, a short message service (SMS) message, a text, an alert, or the like. The patient 102 can review the comparative report 340 on a display of the mobile device 120, or other suitable computing device such as a personal computer. Each patient 102 from among the various patients can access an individualized comparative report 340. The comparative report 340 can include one or more graphs or otherwise be a graphical report.

The rehabilitation portal 220 allows the patient 102 to see how their ROM data 142 (of FIG. 1) compares with a group of patients 102 who had surgery in their community on the same day and/or similar time period. The group of patients 102 can attend therapy together in the same hospital (e.g., 205 of FIG. 2). The rehabilitation portal 220 allows this community to continue into the post discharge time. The rehabilitation portal 220 allows patients 102 to compare their overall functional level with the group of patients 102. In addition, the rehabilitation portal 220 can motivate patients to be more active. For example, a patient 102 can be consoled or motivated by the fact that other patients 102 are going through similar experiences, and are finding the courage to overcome their challenges. The rehabilitation portal 220 allows the patients 102 to communicate among each other in a private and/or anonymous fashion.

The rehabilitation portal 220 can include a client-side application (e.g., 350 and 355) that can be installed on the various mobile devices (e.g., 370 and 375), respectively. The client-side application 350 on the mobile device 370 can automatically receive musculoskeletal rehabilitation information (e.g., 148 of FIG. 1) associated with a particular patient 102 via a short-range wireless connection 352 from an intelligent musculoskeletal rehabilitation apparatus 108. Similarly, the client-side application 355 can automatically receive musculoskeletal rehabilitation information (e.g., 148 of FIG. 1) associated with a different patient 102 via a different short-range wireless connection 362 from a different intelligent musculoskeletal rehabilitation apparatus 108.

The rehabilitation portal 220 can include a server-side application 360 operable on the remote server 130. The client-side application 350 of the rehabilitation portal 220 can aggregate the musculoskeletal rehabilitation information 148 associated with the particular patient 102, and cause the aggregated musculoskeletal rehabilitation information 164 to be transmitted, via a first long-range cellular connection 354, to the server-side application 360 operable on the remote server 130. Similarly, the client-side application 355 of the rehabilitation portal 220 can aggregate the musculoskeletal rehabilitation information 148 associated with the different patient 102, and cause the aggregated musculoskeletal rehabilitation information 164 to be transmitted, via a different long-range cellular connection 364, to the server-side application 360 operable on the remote server 130.

Accordingly, the rehabilitation portal 220 can include client-side applications that are distributed across multiple mobile devices and patients, which can gather the musculoskeletal rehabilitation information 148 via short-range wireless connections. Moreover, the rehabilitation portal 220 can include a server-side application 360, which can communicate with the various client-side applications. The server-side application 360 can produce one or more reports, process the information, aggregate the information, coordinate communities among the patients and the healthcare professionals, or the like.

Figure 4:
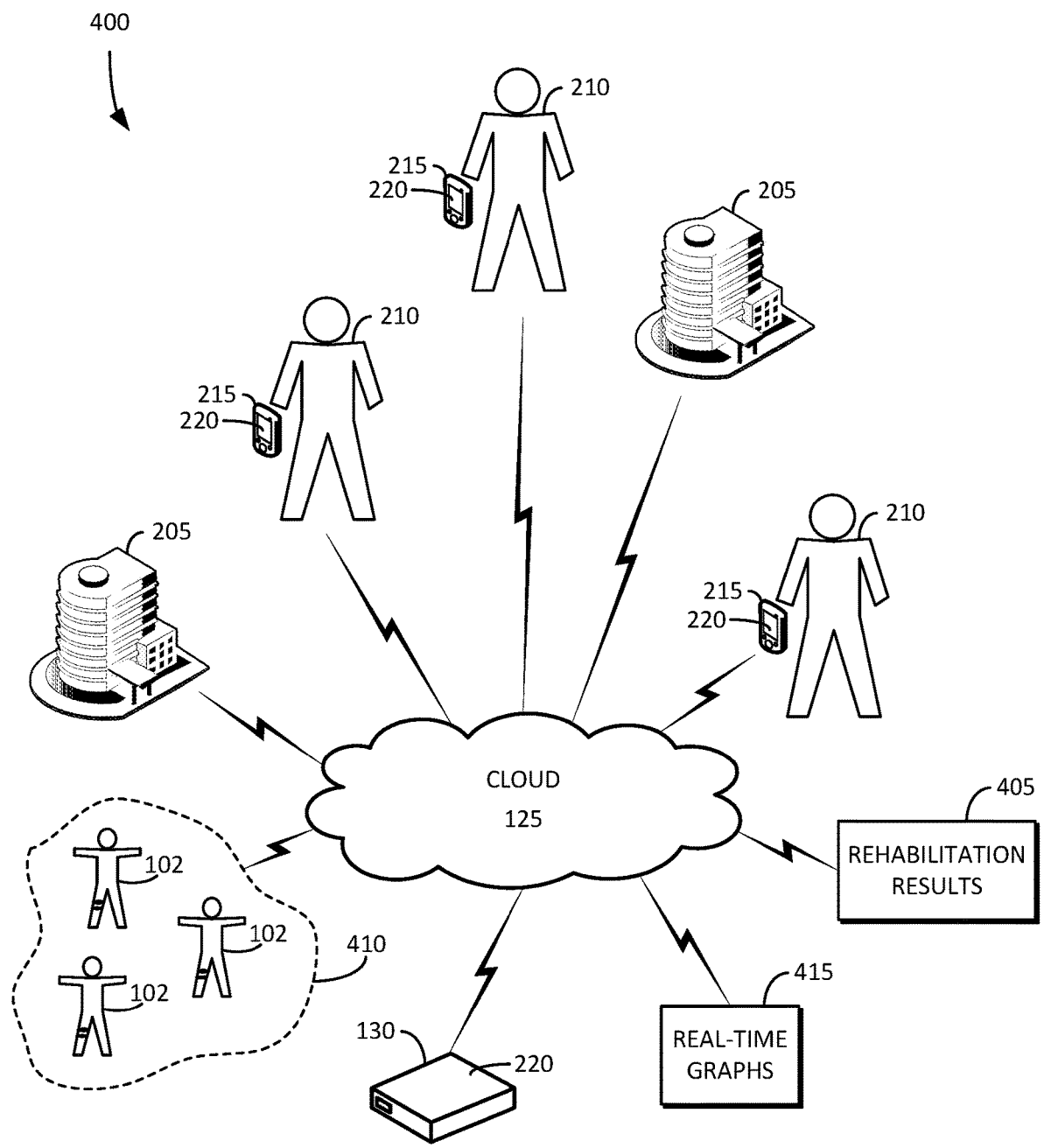
FIG. 4 illustrates still another diagram of an example cloud-assisted system for musculoskeletal rehabilitation in accordance with various embodiments of the present invention.

FIG. 4 illustrates still another diagram of an example cloud-assisted system 400 for musculoskeletal rehabilitation in accordance with various embodiments of the present invention. Using the rehabilitation portal 220, healthcare providers 210 can compare rehabilitation results 405 for certain implants, patient types, and post-operative protocols with each other. This allows real-time evaluation of changes in surgical techniques and therapy, yielding much faster test-change-retest cycles relative to the 3 to 5 year conventional process for a study to be completed and published.

The rehabilitation results 405 can be de-identified. For example, the rehabilitation portal 220 can collect and de-identify the rehabilitation results 405 on multiple patients 102. In other words, information that personally identifies the patients 102, for example, by name or other personally or sensitive identifying information, can be removed or otherwise hidden from view. The de-identified rehabilitation results 405 can be shared among the healthcare providers 210, hospitals 205, or the like. The rehabilitation portal 220 can allow healthcare providers 210 to 'tag' their patients 120 with certain criteria that place them in sub-groups (e.g., 410) for data analysis.

Real-time graphs 415 of patient outcomes (e.g., 144 of FIG. 1) for a particular healthcare provider's patients relative to the other healthcare providers using the rehabilitation portal 220 can be communicated through the rehabilitation portal 220 portal. Alternatively or in addition, the real-time graphs 415 can be pushed to the healthcare providers 210, for example, in an email, a short message service (SMS) message, a text, an alert, or the like. The healthcare providers 210 can review the real-time graphs 415 on a display of the mobile device 215. The rehabilitation portal 220 can provide a network for the healthcare providers 210 to discuss changes in operative techniques and postoperative protocols.

Figure 5:
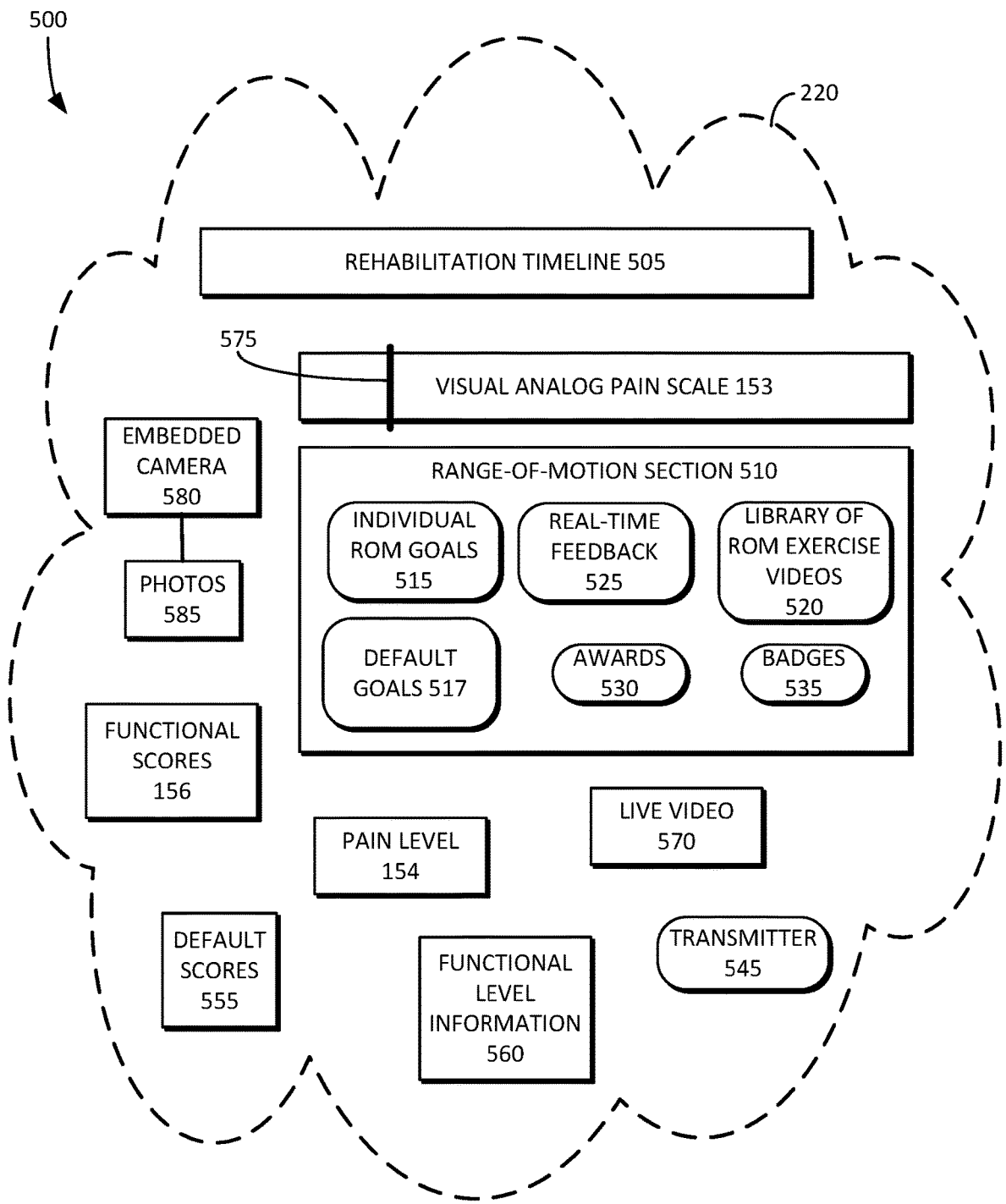
FIG. 5 illustrates examples of components and information associated with a rehabilitation portal for rehabilitating musculoskeletal conditions.

FIG. 5 illustrates a diagram 500 including examples of components and information associated with a rehabilitation portal for rehabilitating musculoskeletal conditions. The rehabilitation portal 220 can include these techniques and/or components. For example, pertaining to rehabilitation exercise instruction, the rehabilitation portal 220 can include a rehabilitation timeline 505. The entire rehabilitation process, or a portion thereof, can be visible as a timeline on the rehabilitation timeline 505. For surgeries, the rehabilitation timeline 505 can include a preoperative and post-operative time period. The rehabilitation progress of the patient 102 can be shown on the rehabilitation timeline 505. All or a portion of the rehabilitation timeline 505 can be presented on a touch-sensitive display of mobile devices 120 and/or 215 (of FIG. 2). The rehabilitation timeline 505 can be scrolled by swiping gestures of a finger or stylus, for example, by the patient's finger or a representative of the healthcare provider's finger. The rehabilitation timeline 505 can be zoomed in or zoomed out to reveal more or less detailed information, respectively. The rehabilitation portal 220 can receive the gestures, process them, and cause the rehabilitation timeline 505 to respond accordingly.

The rehabilitation portal 220 can include a ROM section 510. The ROM section 510 can include individual ROM goals 515 for each patient 102. The individual ROM goals 515 can be chosen individually by the healthcare provider 205 for each patient. Alternatively or in addition, the healthcare provider can choose a default set of goals 517 for each procedure that are automatically assigned to the patient 102. The rehabilitation portal 220 can include a library of ROM exercise videos 520 that can be assigned to the patients 102 to assist in achieving the goals 515 and/or 517. The videos 520 can include a short explanation of the exercise followed by a follow-along video to help the patient 102 to complete the exercise at the correct speed and technique. The rehabilitation portal 220 can change or adapt the ROM goals 515 and/or the exercise videos 520 as the patient 102 achieves each goal or completes a certain set of exercises. The rehabilitation portal 220 can allow the patient 102 to move backward to easier exercises if the visual analog pain scale (e.g., 153 of FIG. 1) shows excessive pain during previous exercise sessions.

Awards 530 and/or badges 535 can be awarded as patients meet certain goals 515 or sets of exercises. The awards 530 can include congratulatory messages, coupons, or the like. The badges 535 can include physical badges and/or icon badges awarded through the rehabilitation portal 220 and displayed on the screen of the mobile device (e.g., 120 of FIG. 2). A real-time graphical display of the ROM data 142 (of FIG. 1) can be provided for real-time feedback 525 on, for example, the amount of flexion and extension obtained. The ROM data 142 can be transmitted to the healthcare provider 210 by transmitter 545. The exercise data 168 (of FIG. 1) including, for example, the number of movement repetitions, can be transmitted to the healthcare provider 210 by the transmitter 545. The time spent exercising can be transmitted to the healthcare provider 210 by the transmitter 545. The transmitter 545 can be included, for example, in the mobile device 120 (of FIG. 1). Moreover, the transmitter 545 can transmit information such as the pain level 154, the functional scores 156, and the like, as described in detail above.

The functional scores 156 that are specific to joint surgery performed can be made available to the healthcare provider 210 in the rehabilitation portal 220. The healthcare provider 210 can customize when a score is required for each surgery. Alternatively or in addition, the healthcare provider 210 can choose a default set of scores 555 built into or otherwise predefined by the rehabilitation portal 220.

At designated times, patients can be prompted to answer questions based on the default scores 555 selected by the healthcare provider 210. Such default scores 555 can be returned to the rehabilitation portal 220 where they can be saved for the patient 102 and available for recovery based on the patient 102, the healthcare provider 210, a group of patients, and/or a group of healthcare providers.

At the beginning of the rehabilitation program, the patient 102 can be asked by the rehabilitation portal 220 to rate their pain using the visual analog pain scale 153. The visual analog pain scale 153 can include a slider bar 575 with one side of the scale 153 (e.g., the left side) being no pain and the other side of the scale 153 (e.g., the right side) being the worst pain they have ever experienced. At the beginning and at the end of each session, the patient 102 can be asked by the rehabilitation portal 220 to use the visual analog pain scale 153 to rate the pain they had prior to the session and/or during the session. The pain data can be displayed in the rehabilitation portal 220 to allow the patient 102 to see their progress and understand if they are pushing too hard during the sessions. The pain data can be transmitted to and/or stored by the rehabilitation portal 220 for later retrieval.

The rehabilitation portal 220 can measure and store functional level information 560. For example, the rehabilitation portal 220 can measure how active the patient is during the day. The rehabilitation portal 220 can communicate with the intelligent musculoskeletal rehabilitation apparatus 108 (of FIG. 1). The intelligent musculoskeletal rehabilitation apparatus 108 can measure how active the patient is during the day, and communicate such functional level information 560 to the rehabilitation portal 220. The functional level information 560 can be saved and/or graphically displayed through the rehabilitation portal 220 relative to previous data for the patient 102. Alternatively or in addition, the functional level information 560 can be saved and/or graphically displayed through the rehabilitation portal 220 relative to previous crowd sourced data from other patients 102 and/or healthcare providers 210, for example, having the same or similar postoperative date.

The rehabilitation portal 220 can cause an embedded camera 580, which can be part of the mobile device 120 (e.g., smart phone or tablet) to take one or more photos 585 of the patient's incision, wound, and/or injury. The rehabilitation portal 220 can prompt the patient 102 to take the photos 585. The patient 102 can be prompted to take the one or more photos 585 at times defined by the healthcare provider 210 in the rehabilitation portal 220. The healthcare provider 210 can be provided with the option to request the one or more photos 585 at additional times if needed. Alternatively or in addition, the patient 102 can take the one or more photos 585 and send them to the healthcare provider 210 through the rehabilitation portal 220 at any desired time.

The healthcare providers 210 can video-chat via live video 570 with the patient 102 using the rehabilitation portal 220 rather than requiring that the patient 102 to physically come to the office for a follow up visit. The healthcare provider 210 can have all the patients' ROM data 142 (of FIG. 1) and functional data (e.g., 156 of FIG. 1 and 560 of FIG. 5) in the rehabilitation portal 220 as well as the one or more photos 585 of the patient's incision, wound, and/or injury easily and quickly available. In the case of a post-operative patient, this is a significant time saving feature as surgeons do not get paid any additional amount for visits in the first 90 days after surgery. Moreover, post-operative patients find it difficult to travel to the office. The video-chat session can be scheduled through the rehabilitation portal 220 and an invitation can be sent to the patient 102.

Figure 6:
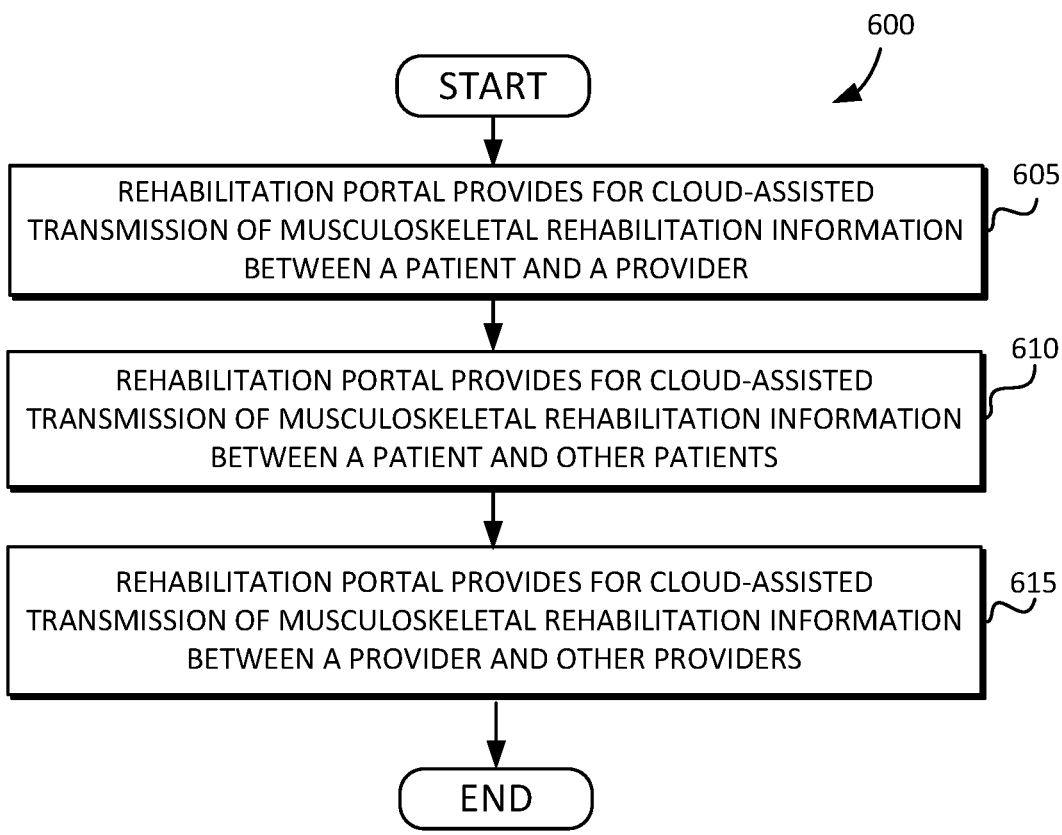
FIG. 6 is a flow diagram illustrating a technique for cloud-assisted transmission of musculoskeletal rehabilitation information according to various embodiments of the present invention.

FIG. 6 is a flow diagram 600 illustrating a technique for cloud-assisted transmission of musculoskeletal rehabilitation information according to various embodiments of the present invention. The flow begins at 605 where a rehabilitation portal (e.g., 220 of FIG. 2) provides for cloud-assisted transmission of musculoskeletal rehabilitation information (e.g., 164 of FIG. 1) between a patient (e.g., 102 of FIG. 1) and a provider (e.g., 210 of FIG. 2). The flow proceeds to 610 where the rehabilitation portal 220 can provide for cloud-assisted transmission of musculoskeletal rehabilitation information (e.g., 164) between a patient (e.g., 102 of FIG. 1) and other patients (e.g., 102 of FIG. 3). At 615, the rehabilitation portal 220 can provide for cloud-assisted transmission of musculoskeletal rehabilitation information (e.g., 164) between a provider (e.g., 210 of FIG. 2) and other providers (e.g., 210 of FIG. 4). It will be understood that the steps need not occur in the illustrated order, but rather, can occur in a different order or with intervening steps.

Figure 7:
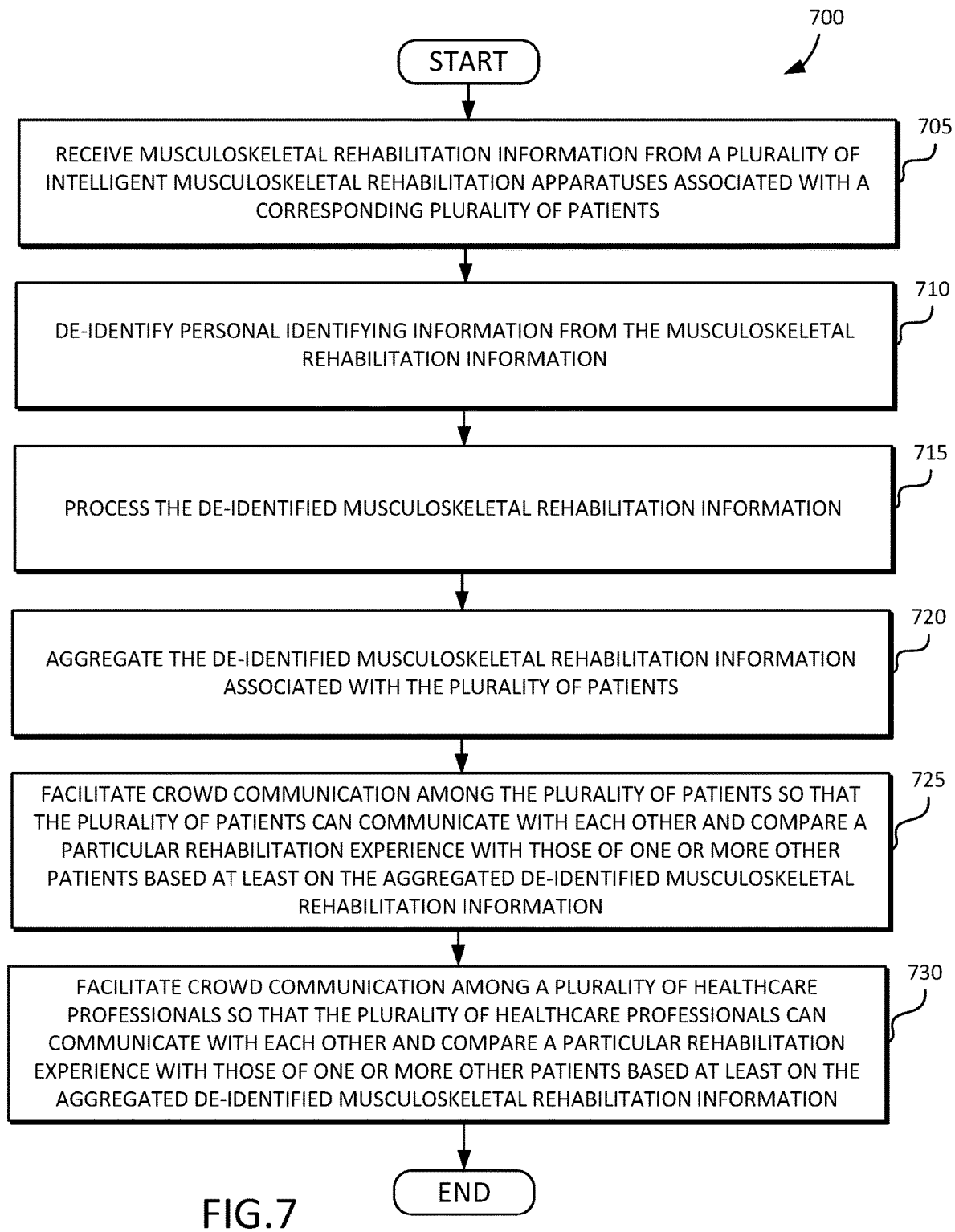
FIG. 7 is another flow diagram illustrating another technique for cloud-assisted transmission of musculoskeletal rehabilitation information according to various embodiments of the present invention.

FIG. 7 is another flow diagram 700 illustrating another technique for cloud-assisted transmission of musculoskeletal rehabilitation information according to various embodiments of the present invention.

The technique for rehabilitating patients having musculoskeletal conditions can begin at 705, where musculoskeletal rehabilitation information from a plurality of intelligent musculoskeletal rehabilitation apparatuses associated with a corresponding plurality of patients can be received by a rehabilitation portal. At 710, personal identifying information can be de-identified, by the rehabilitation portal, from the musculoskeletal rehabilitation information. At 715, the de-identified musculoskeletal rehabilitation information can be processed, by the rehabilitation portal. At 720, the de-identified musculoskeletal rehabilitation information associated with the plurality of patients can be aggregated, by the rehabilitation portal. At 725, crowd communication among the plurality of patients can be facilitated, by the rehabilitation portal, so that the plurality of patients can communicate with each other and compare a particular rehabilitation experience with those of one or more other patients from among the plurality of patients based at least on the aggregated de-identified musculoskeletal rehabilitation information. At 730, crowd communication among a plurality of healthcare professionals can be facilitated, by the rehabilitation portal, so that the plurality of healthcare professionals can communicate with each other and compare a particular rehabilitation experience with those of one or more other patients from among the plurality of patients based at least on the aggregated de-identified musculoskeletal rehabilitation information.

Figure 8A:
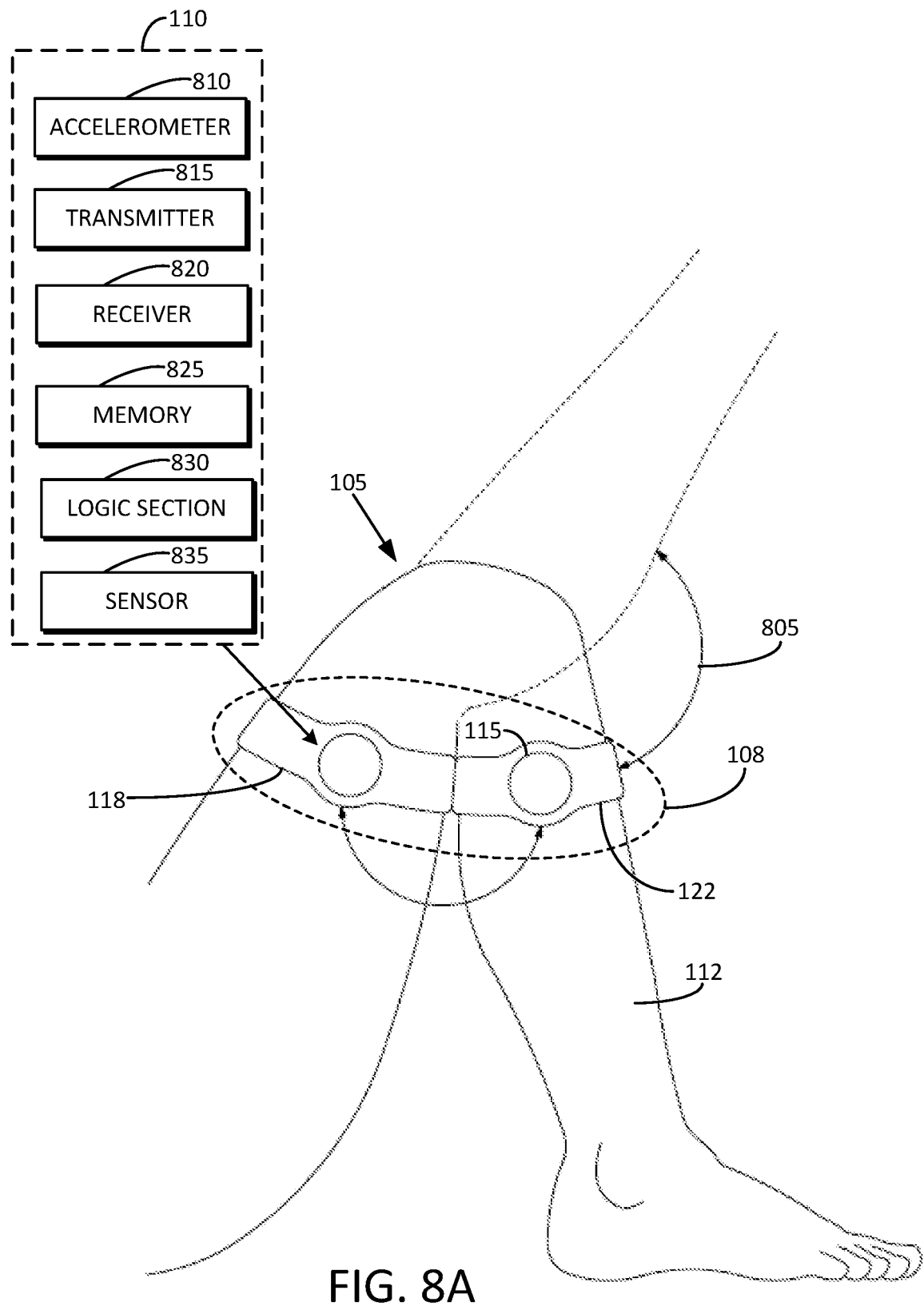

FIGS. 8A-8C illustrate example embodiments of an intelligent musculoskeletal rehabilitation apparatus according to some embodiments of the present invention. The intelligent musculoskeletal rehabilitation apparatus 108 can be comprised of individual and separate intelligent rehabilitation members (e.g., 110 and 115) that can be electronically paired to each other, as further described below. The intelligent musculoskeletal rehabilitation apparatus 108 can be configured such that it allows low-friction extension of a limb (e.g., 112) at the joint 105 as shown at 805.

The intelligent musculoskeletal rehabilitation apparatus 108 can include one or more accelerometers 810, one or more transmitters 815, one or more receivers 820, memory 825, a logic section 830, one or more sensors 835, or the like. For example, one or more of the intelligent rehabilitation members (e.g., 110 and 115) can include the one or more accelerometers 810, the one or more transmitters 815, the one or more receivers 820, the memory 825, the logic section 830, the one or more sensors 835, or the like. It will be understood that each of the one or more intelligent rehabilitation members (e.g., 110, 115, 132, 134, and/or 136 of FIG. 1) of the intelligent musculoskeletal rehabilitation apparatus 108 can include the one or more accelerometers 810, the one or more transmitters 815, the one or more receivers 820, the memory 825, the logic section 830, the one or more sensors 835, or the like.

In some embodiments, one of the intelligent rehabilitation members (e.g., 115) can include fewer components than another of the intelligent rehabilitation members (e.g., 110). For example, the intelligent rehabilitation member 115 can include the one or more accelerometers 810, the one or more sensors 835, and the one or more transmitters 815, but need not include the one or more receivers 820. Alternatively, the intelligent rehabilitation member 115 can include the one or more sensors 835 and the one or more transmitters 815, but not the other components, and so forth. In this manner, a designated intelligent rehabilitation member 110 can be the primary member to communicate with the mobile device (e.g., 120 of FIG. 1), and one or more other intelligent rehabilitation members (e.g., 115) can gather rehabilitation data and transmit it to the primary member 110.

FIG. 8B illustrates a front view of the limb 112, the joint 105, and the intelligent musculoskeletal rehabilitation apparatus 108 according to an embodiment. FIG. 8C illustrates a back view of the limb 112, the joint 105, and the intelligent musculoskeletal rehabilitation apparatus 108 according to an embodiment. In some embodiments, the intelligent rehabilitation members 110 and 115 can be positioned on a front side of the limb 112 as shown in FIG. 8B, or on a side of the limb 112 as shown in FIG. 8A. It will be understood that the intelligent musculoskeletal rehabilitation apparatus 108 can be attached to any suitable location of the body of the patient 102, as described above. It will also be understood that the dimensions of the straps (e.g., 118 and 122) and the dimensions of the intelligent rehabilitation members (e.g., 110 and 115) of the intelligent musculoskeletal rehabilitation apparatus 108 can be different (e.g., increased or decreased) depending on which area of the body of the patient 102 these are attached.

Referring to FIG. 8C, attachment means 805 can include a sliding buckle 810, for example, toward one end of the strap 122, and through which another end of the strap 122 can be threaded. The strap 122 can then be doubled back on itself and secured using the Velcro® 815 or other suitable fastener. In some embodiments, the intelligent rehabilitation members 110 and 115 can each be secured to the patient 102 using the same or similar attachment means 805.

Figure 9A:
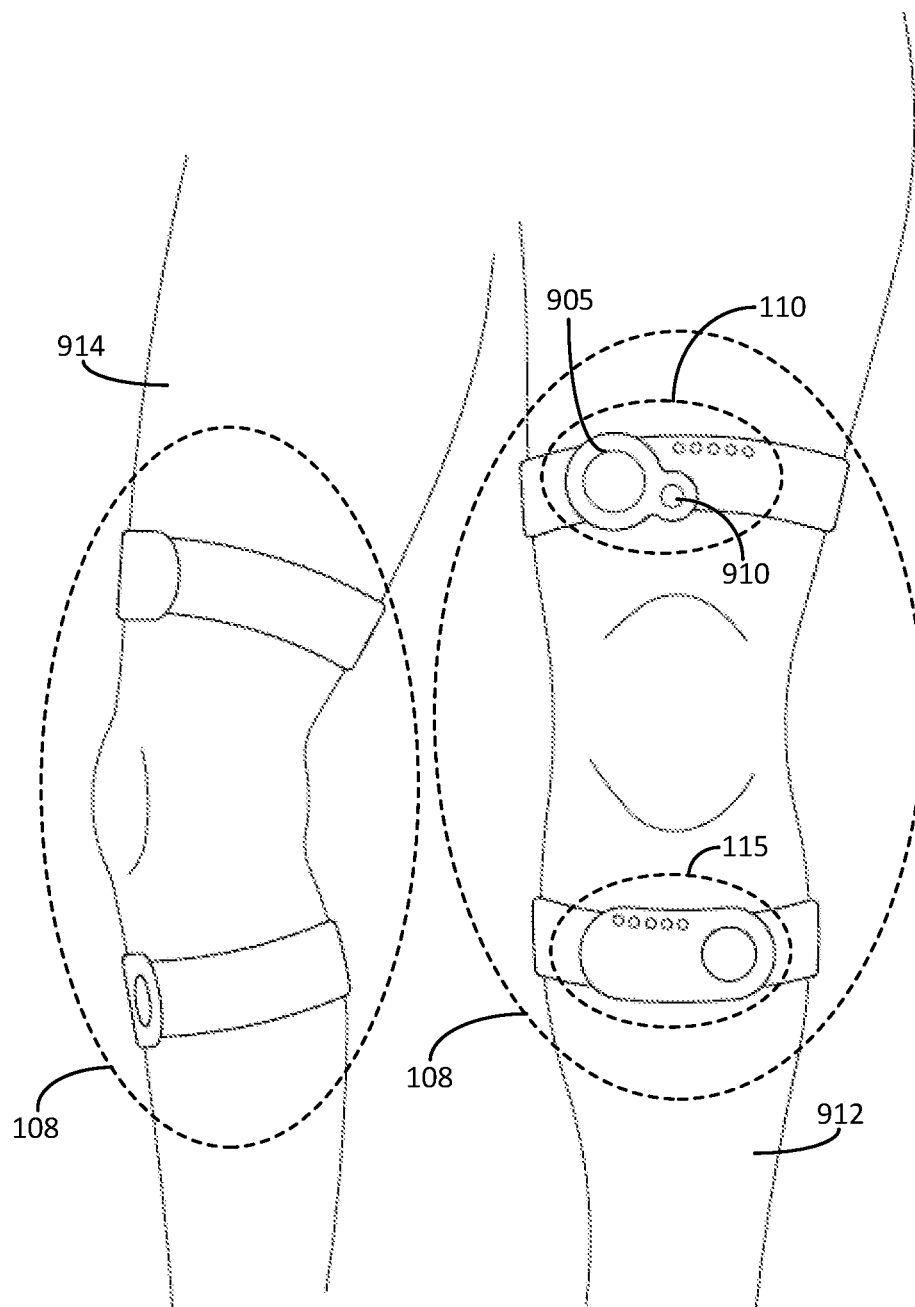
FIG. 9A illustrates example embodiments of an intelligent musculoskeletal rehabilitation apparatus according to some embodiments of the present invention.
Figure 9B:
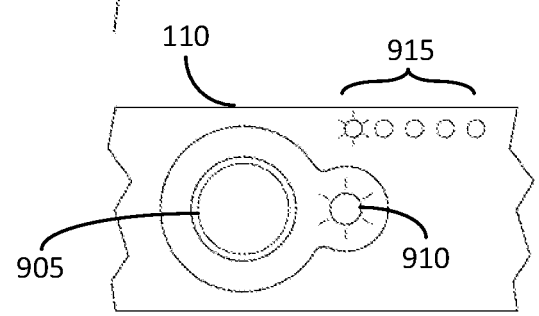
FIG. 9B illustrates a close-up view of an intelligent rehabilitation member.

FIG. 9A illustrates example embodiments of an intelligent musculoskeletal rehabilitation apparatus 108 according to some embodiments of the present invention. FIG. 9B illustrates a close-up view of an intelligent rehabilitation member 110. Reference is now made to FIGS. 9A and 9B.

The patient can have multiple intelligent musculoskeletal rehabilitation apparatuses 108 attached to his or her body. For example, the limb 914 can have an intelligent musculoskeletal rehabilitation apparatus 108 attached thereto, and the limb 912 can have a different intelligent musculoskeletal rehabilitation apparatus 108 attached thereto. Each of the intelligent musculoskeletal rehabilitation apparatuses 108 can have one or more intelligent rehabilitation members (e.g., 110 and 115). The intelligent rehabilitation member 110 can include an actuator 905 for pairing the intelligent rehabilitation members (e.g., 110 and 115). It will be understood that two or more intelligent rehabilitation members can be paired, or otherwise grouped into a logical group. Alternatively or in addition, the intelligent rehabilitation member 115 can include an actuator 905 for pairing the intelligent rehabilitation members. The intelligent rehabilitation member (e.g., 110 or 115) can include an indicator 910 for indicating that the pairing has completed. The indicator can be a visual and/or audible indicator. The intelligent rehabilitation member (e.g., 110 or 115) can include a battery level indicator 915 to indicate a level of charge left on the battery.

Put differently, the intelligent rehabilitation member 110 can include an actuator 905 for creating a logical pairing between the intelligent rehabilitation member 110 and the intelligent rehabilitation member 115. The intelligent rehabilitation member 110 can include the paired indicator 910 to indicate whether or not the logical pairing between the intelligent rehabilitation member 110 and the intelligent rehabilitation member 115 has occurred. While each of the intelligent rehabilitation members (e.g., 110 and 115) can gather musculoskeletal rehabilitation information (e.g., 148 of FIG. 1), one of the intelligent rehabilitation members (e.g., 110) can be designated the primary member for gathering the musculoskeletal rehabilitation information 142 for a particular intelligent musculoskeletal rehabilitation apparatus 108, and transmitting the musculoskeletal rehabilitation information 142 for the particular intelligent musculoskeletal rehabilitation apparatus 108 to the mobile device (e.g., 120 of FIG. 1).

Figure 10A:
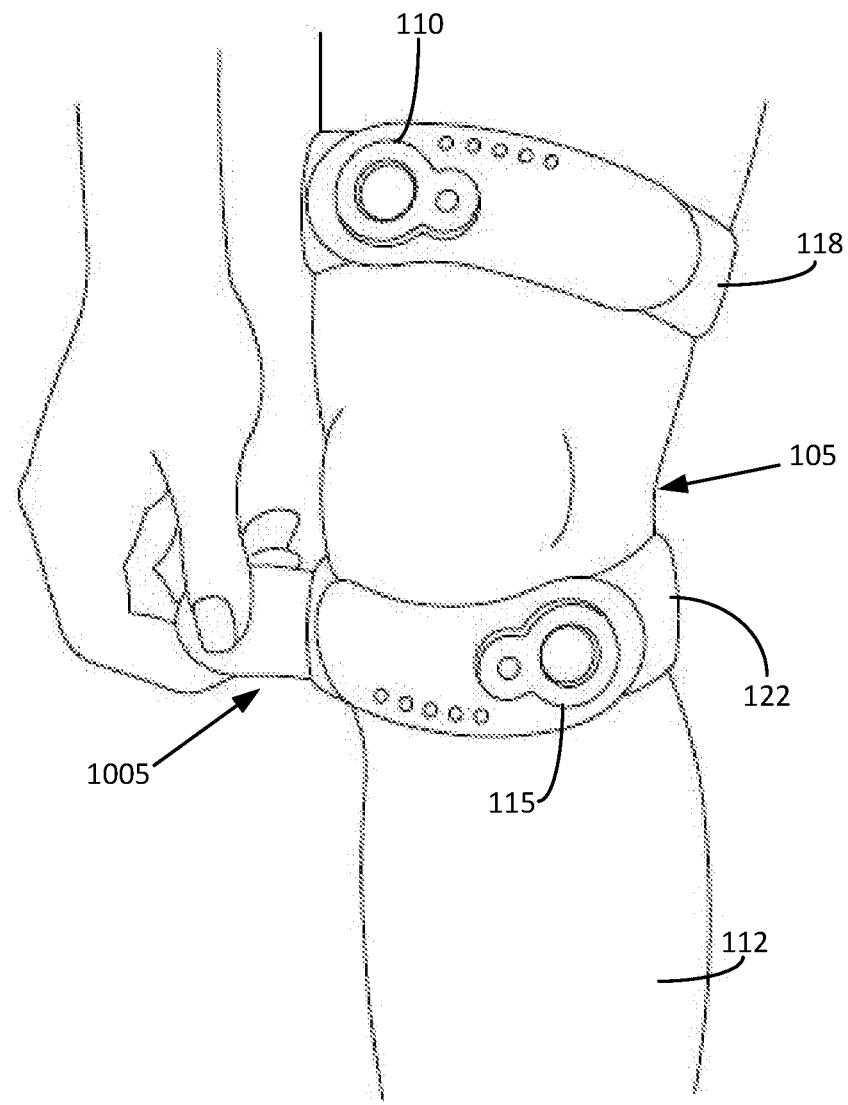
FIGS. 10A-10C illustrate example embodiments of an intelligent musculoskeletal rehabilitation apparatus according to some embodiments of the present invention.
Figures 10B, 10C:
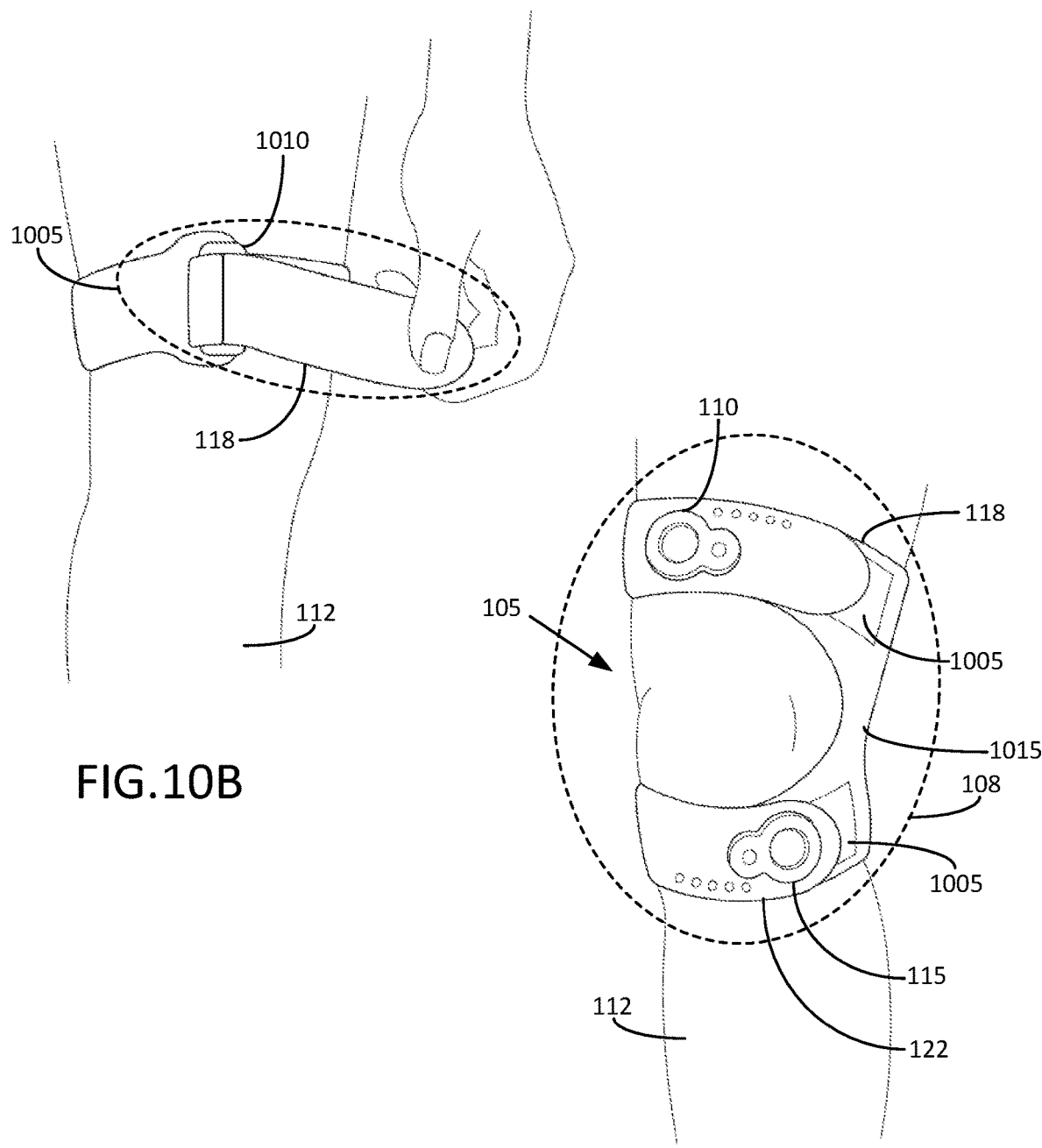

FIGS. 10A-10C illustrate example embodiments of an intelligent musculoskeletal rehabilitation apparatus according to some embodiments of the present invention. FIG. 10A illustrates the limb 112 and joint 105. The strap 122 of the intelligent musculoskeletal rehabilitation apparatus 108 can include attachment means 1005 for attaching the strap 122 and the intelligent rehabilitation member 115 to the limb 112. The attachment means 1005 can include, for example, a sliding buckle. Alternatively or in addition, the attachment means 1005 can include Velcro® or other suitable fastener.

The strap 122 can be inserted through the sliding buckle, and then secured using the Velcro® or other suitable fastener to the strap 122 itself. Similarly, the strap 118 can include the same or similar attachment means 1005 for attaching the intelligent rehabilitation member 110 to the limb 112, for example, above the joint 105.

As shown in FIG. 10B, the attachment means 1005 can include a sliding buckle 1010 toward one end of the strap 118, and through which another end of the strap 118 can be threaded. The strap 118 can then be doubled back on itself and secured using the Velcro® or other suitable fastener.

In some embodiments, the intelligent musculoskeletal rehabilitation apparatus 108 can be comprised of a single contiguous whole. FIG. 10C illustrates the intelligent musculoskeletal rehabilitation apparatus 108 as a single contiguous whole. The strap 122 of the intelligent musculoskeletal rehabilitation apparatus 108 can be connected to the strap 118 via a body and/or hinge section 1015. The strap 122 of the intelligent musculoskeletal rehabilitation apparatus 108 can include attachment means 1005 for attaching the strap 122 and the intelligent rehabilitation member 115 to the lower limb 112, for example, below the joint 105. The attachment means 1005 can include, for example, Velcro® or other suitable fastener. Similarly, the strap 118 can include the same or similar attachment means 1005 for attaching the intelligent rehabilitation member 110 to the upper limb 112, for example, above the joint 105.

It will be understood that while detailed views of the intelligent musculoskeletal rehabilitation apparatus 108 are provided with respect to a knee joint and a leg, the rehabilitation apparatus 108 can be secured to the patient 102 at various different locations of the body as described above with reference to FIG. 1 using the same or similar attachment means.

Reference is now made to FIGS. 1 through 10C. Embodiments of the present invention include a cloud-assisted rehabilitation system for musculoskeletal conditions. The cloud-assisted rehabilitation system can include a plurality of intelligent musculoskeletal rehabilitation apparatuses 108 each including one or more intelligent rehabilitation members (e.g., 110, 115, 132, 134, and/or 136). Each of the intelligent rehabilitation members can include a logic section 830. The intelligent musculoskeletal rehabilitation apparatuses 108 can be attached to a corresponding plurality of patients 102 to generate, by the corresponding logic section 830, musculoskeletal rehabilitation information 148.

The cloud-assisted rehabilitation system can include a rehabilitation portal 220 to receive the musculoskeletal rehabilitation information 148 from the plurality of patients 102, de-identify personal identifying information from the musculoskeletal rehabilitation information 148, process the musculoskeletal rehabilitation information 148, aggregate the de-identified musculoskeletal rehabilitation information 148 to produce aggregated de-identified musculoskeletal rehabilitation information 164, and generate one or more reports (e.g., 235, 310, 340) for one or more healthcare professionals 210 based at least on the aggregated de-identified musculoskeletal rehabilitation information 164.

The rehabilitation portal 220 can facilitate crowd communication among the plurality of patients 102 so that the plurality of patients 102 can communicate with each other and compare a particular rehabilitation experience with one or more other patients 102 from among the plurality of patients 102 based at least on the aggregated de-identified musculoskeletal rehabilitation information 164.

The rehabilitation portal 220 can facilitate crowd communication among a plurality of healthcare professionals 210 so that the plurality of healthcare professionals 210 can communicate with each other and compare a particular rehabilitation experience with one or more other patients 102 from among the plurality of patients 102 based at least on the aggregated de-identified musculoskeletal rehabilitation information 164.

The rehabilitation portal 220 can include a first client-side application (e.g., 350) operable on a first mobile device (e.g., 370). The first client-side application 350 can automatically receive first musculoskeletal rehabilitation information 148 associated with a first patient 102 via a short-range wireless connection 352 from a first intelligent musculoskeletal rehabilitation apparatus 108.

The rehabilitation portal 220 can include a second client-side application (e.g., 355) operable on a second mobile device (e.g., 375). The second client-side application 355 can automatically receive second musculoskeletal rehabilitation information associated with a second different patient via a short-range wireless connection 362 from a second intelligent musculoskeletal rehabilitation apparatus 108. It will be understood that any suitable number of patients, client-side applications, and corresponding intelligent musculoskeletal rehabilitation apparatuses can be included in the system.

The first client-side application 350 can receive third musculoskeletal rehabilitation information (e.g., 154, 156, 144) associated with the first patient 102 via a manual entry of the third musculoskeletal rehabilitation information using a touch-sensitive screen 158 of the first mobile device 370. The second client-side application 355 can receive fourth musculoskeletal rehabilitation information (e.g., 154, 156, 144) associated with the second patient 102 via a manual entry of the fourth musculoskeletal rehabilitation information using a touch-sensitive screen 158 of the second mobile device 375.

The cloud-assisted rehabilitation system can include a remote server 130. The rehabilitation portal 220 can include a server-side application 360 operable on the remote server 130. The first client-side application 350 of the rehabilitation portal 220 can aggregate the first and third musculoskeletal rehabilitation information associated with the first patient 102, and to cause the aggregated first and third musculoskeletal rehabilitation information (e.g., 148, 154, 156, 144) to be transmitted, via a first long-range cellular connection 354, to the server-side application 360 operable on the remote server 130. The second client-side application 355 of the rehabilitation portal 220 can aggregate the second and fourth musculoskeletal rehabilitation information (e.g., 148, 154, 156, 144) associated with the second patient 102, and cause the aggregated second and fourth musculoskeletal rehabilitation information to be transmitted, via a second long-range cellular connection 364, to the server-side application 360 operable on the remote server 130.

The rehabilitation portal 220 can include the server-side application 360 operable on the remote server 130. The server-side application 360 can receive and aggregate the first and third musculoskeletal rehabilitation information (e.g., 148, 154, 156, 144) associated with the first patient 102, and the second and fourth musculoskeletal rehabilitation information (e.g., 148, 154, 156, 144) associated with the second patient 102, and to generate the one or more reports (e.g., 235, 310, 340) based at least on the aggregated first, second, third, and fourth musculoskeletal rehabilitation information.

Each of the intelligent rehabilitation members (e.g., 110, 115, 132, 134, and/or 136) associated with corresponding intelligent musculoskeletal rehabilitation apparatuses 108 can include a transmitter 815, a first accelerometer 810, a first sensor 835, and a memory 825. In some embodiments, an intelligent rehabilitation member (e.g., 115) associated with a particular intelligent musculoskeletal rehabilitation apparatus 108 can include a second accelerometer (e.g., such as 810) and a second sensor (e.g., such as 835). The logic section 830 of a first intelligent rehabilitation member (e.g., 110) can automatically gather at least some of (e.g., a first portion of) the musculoskeletal rehabilitation information 148 using at least one of the first accelerometer 810 or the first sensor 835. The logic section of a second intelligent rehabilitation member (e.g., 815) can automatically gather at least some of (e.g., a second portion of) the musculoskeletal rehabilitation information 148 using at least one of the second accelerometer or the second sensor.

The logic section 830 of the first intelligent rehabilitation member 110 can store the gathered musculoskeletal rehabilitation information, gathered by both the first and second intelligent rehabilitation members 110 and 115, in the memory 825 of the first intelligent rehabilitation member 110. The logic section of the first intelligent rehabilitation member 110 can cause the transmitter 815 to transmit the gathered musculoskeletal rehabilitation information 148, gathered by both the first and second intelligent rehabilitation members (e.g., 110 and 115), to the rehabilitation portal 220 via a short-range wireless connection (e.g., 352 or 362). It will be understood that the first intelligent rehabilitation member 110 can be designated the primary member from among a plurality of intelligent rehabilitation members, and configured to transmit the aggregated musculoskeletal rehabilitation information 164 to the mobile device 120.

The first intelligent rehabilitation member 110 can include an actuator 905 for creating a logical pairing between the first intelligent rehabilitation member 110 and the second intelligent rehabilitation member 115. The first intelligent rehabilitation member 110 can include a paired indicator 910 to indicate whether or not the logical pairing between the first intelligent rehabilitation member 110 and the second intelligent rehabilitation member 115 has occurred or otherwise been completed. Once paired, the second intelligent rehabilitation member 115 can transmit the musculoskeletal rehabilitation information 148 that it has gathered to the first, primary intelligent rehabilitation member 110, which can itself can transmit all of the musculoskeletal rehabilitation information 148 for a given intelligent musculoskeletal rehabilitation apparatuses 108 to a corresponding mobile device (e.g., 120). The client-side application (e.g., 350) can transmit the musculoskeletal rehabilitation information 148 to the server-side application (e.g., 360) for processing and analysis.

The plurality of intelligent musculoskeletal rehabilitation apparatuses each include one or more intelligent rehabilitation members, as described above. Each of the intelligent rehabilitation members can include one or more sensors and a transmitter. In accordance with embodiments of the present invention, a technique can include gathering, by the one or more sensors, the musculoskeletal rehabilitation information from a corresponding patient from among the plurality of patients. The technique can further include transmitting, by the transmitter, the gathered musculoskeletal rehabilitation information associated with the corresponding patient to a mobile device, from the one or more intelligent rehabilitation members.

The technique can further include automatically receiving, by a first client-side application of the rehabilitation portal operable on a first mobile device, first musculoskeletal rehabilitation information associated with a first patient via a short-range wireless connection from a first intelligent musculoskeletal rehabilitation apparatus from among the plurality of intelligent musculoskeletal rehabilitation apparatuses. The technique can include automatically receiving, by a second client-side application of the rehabilitation portal operable on a second mobile device, second musculoskeletal rehabilitation information associated with a second patient via a short-range wireless connection from a second intelligent musculoskeletal rehabilitation apparatus from among the plurality of intelligent musculoskeletal rehabilitation apparatuses.

The technique can include receiving, by the first client-side application, third musculoskeletal rehabilitation information associated with the first patient via a manual entry of the third musculoskeletal rehabilitation information using a touch-sensitive screen of the first mobile device. The technique can include receiving, by the second client-side application, fourth musculoskeletal rehabilitation information associated with the second patient via a manual entry of the fourth musculoskeletal rehabilitation information using a touch-sensitive screen of the second mobile device.

The technique can include aggregating, by the first client-side application of the rehabilitation portal, the first and third musculoskeletal rehabilitation information associated with the first patient. The technique can include causing to be transmitted, via a first long-range cellular connection, the aggregated first and third musculoskeletal rehabilitation information, to a server-side application of the rehabilitation portal operable on a remote server. The technique can include aggregating, by the second client-side application of the rehabilitation portal, the second and fourth musculoskeletal rehabilitation information associated with the second patient. Moreover, the technique can include causing to be transmitted, via a second long-range cellular connection, the aggregated second and fourth musculoskeletal rehabilitation information, to the server-side application operable on the remote server.

The technique can include receiving, by the server-side application, the first and third musculoskeletal rehabilitation information associated with the first patient, and the second and fourth musculoskeletal rehabilitation information associated with the second patient. The technique can include aggregating, by the server-side application, the first and third musculoskeletal rehabilitation information associated with the first patient, and the second and fourth musculoskeletal rehabilitation information associated with the second patient. The technique can include generating one or more reports based at least on the aggregated first, second, third, and fourth musculoskeletal rehabilitation information.

The various patients 108 and healthcare providers 210 can access the de-identified aggregated musculoskeletal rehabilitation information to assist in patient recovery, data analysis, coordination among healthcare professionals, and perfection of musculoskeletal rehabilitation techniques.

The following discussion is intended to provide a brief, general description of a suitable machine or machines in which certain aspects of the invention can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, watches, glasses, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the invention can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the invention with reference to illustrated embodiments, it will be recognized that the illustrated embodiments can be modified in arrangement and detail without departing from such principles, and can be combined in any desired manner. And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the embodiments as described herein.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

The invention claimed is:

1. A rehabilitation system for musculoskeletal conditions, comprising:
   a rehabilitation portal including a client-side application operable on a mobile device, the client-side application being configured to receive musculoskeletal rehabilitation information associated with a patient via a short-range wireless connection from a musculoskeletal rehabilitation apparatus that is attachable to the patient,
   wherein the rehabilitation portal is configured to automatically receive the musculoskeletal rehabilitation information from the intelligent musculoskeletal rehabilitation apparatus, process the musculoskeletal rehabilitation information, aggregate the musculoskeletal rehabilitation information, and generate one or more reports for one or more healthcare professionals based at least on the aggregated musculoskeletal rehabilitation information.

2. The rehabilitation system for musculoskeletal conditions of claim 1, further comprising:
   a remote server; and
   a server-side application operable on the remote server,
   wherein the client-side application of the rehabilitation portal is configured to cause the musculoskeletal rehabilitation information to be transmitted, via a long-range cellular connection, to the server-side application operable on the remote server.

3. The rehabilitation system for musculoskeletal conditions of claim 2, wherein the rehabilitation portal includes the server-side application, and wherein the server-side application is configured to process the musculoskeletal rehabilitation information, aggregate the musculoskeletal rehabilitation information, and generate the one or more reports for the one or more healthcare professionals based at least on the aggregated musculoskeletal rehabilitation information.

4. The rehabilitation system for musculoskeletal conditions of claim 1, wherein the client-side application that is operable on the mobile device is configured to process the musculoskeletal rehabilitation information, aggregate the musculoskeletal rehabilitation information, and generate the one or more reports for the one or more healthcare professionals based at least on the aggregated musculoskeletal rehabilitation information.

5. The rehabilitation system for musculoskeletal conditions of claim 1, wherein the musculoskeletal rehabilitation apparatus includes one or more members, each of the members having a logic section, wherein the musculoskeletal rehabilitation apparatus is configured to generate, by the logic section, the musculoskeletal rehabilitation information.

6. The rehabilitation system for musculoskeletal conditions of claim 5, wherein:
   the one or more members includes a transmitter and at least one of an accelerometer, a sensor, or a memory;
   the one or more members is attachable to the patient; and
   the logic section is configured to gather the musculoskeletal rehabilitation information about the patient using the at least one of the accelerometer, the sensor, or the memory.

7. The rehabilitation system for musculoskeletal conditions of claim 6, wherein:
   the logic section is configured to store the gathered musculoskeletal rehabilitation information in the memory;

the transmitter is configured to transmit the musculoskeletal rehabilitation information to the rehabilitation portal; and the rehabilitation portal is further configured to facilitate tracking of individual progress of the patient based at least on the transmitted musculoskeletal rehabilitation information.

8. The rehabilitation system for musculoskeletal conditions of claim 1, wherein:

the musculoskeletal rehabilitation information is first musculoskeletal rehabilitation information; and the client-side application is configured to receive second musculoskeletal rehabilitation information associated with the patient via a manual entry of the second musculoskeletal rehabilitation information using a touch-sensitive screen of the mobile device.

9. The rehabilitation system for musculoskeletal conditions of claim 1, wherein:

the musculoskeletal rehabilitation apparatus includes a first member that is configured to gather first musculoskeletal rehabilitation information associated with the patient;

the musculoskeletal rehabilitation apparatus includes a second member that is configured to gather second musculoskeletal rehabilitation information associated with the patient; and the rehabilitation portal is configured to receive and aggregate the first and second musculoskeletal rehabilitation information associated with the patient, and to generate the one or more reports based at least on the aggregated first and second musculoskeletal rehabilitation information.

10. The rehabilitation system for musculoskeletal conditions of claim 1, wherein the rehabilitation portal is configured to de-identify personal identifying information from the musculoskeletal rehabilitation information, process the de-identified musculoskeletal rehabilitation information, aggregate the de-identified musculoskeletal rehabilitation information, and generate the one or more reports for the one or more healthcare professionals based at least on the aggregated de-identified musculoskeletal rehabilitation information.

11. The rehabilitation system for musculoskeletal conditions of claim 1, wherein:

the musculoskeletal rehabilitation apparatus includes a first intelligent rehabilitation member and a second intelligent rehabilitation member;

the first intelligent rehabilitation member is attachable to the patient, and includes a first logic section, a first transmitter, a first accelerometer, a first sensor, and a first memory;

the second intelligent rehabilitation member is attachable to the patient, and includes a second logic section, a second transmitter, a second accelerometer, a second sensor, and a second memory;

the first logic section of the first intelligent rehabilitation member is configured to gather a first portion of the musculoskeletal rehabilitation information about the patient using at least one of the first accelerometer, the first sensor, or the first memory;

the second logic section of the second intelligent rehabilitation member is configured to gather a second portion of the musculoskeletal rehabilitation information about the patient using at least one of the second accelerometer, the second sensor, or the second memory;

the first logic section is configured to store the first portion of the gathered musculoskeletal rehabilitation information in the first memory;

the second logic section is configured to store the second portion of the gathered musculoskeletal rehabilitation information in the second memory;

the first transmitter is configured to transmit the first portion of the musculoskeletal rehabilitation information to the second intelligent rehabilitation member;

the second transmitter is configured to transmit the first portion and the second portion of the musculoskeletal rehabilitation information to the rehabilitation portal; and the rehabilitation portal is further configured to facilitate tracking of individual progress of the patient based at least on the transmitted first portion and the transmitted second portion of the musculoskeletal rehabilitation information.

12. A method for rehabilitating patients having musculoskeletal conditions, the method comprising:

generating, by a musculoskeletal rehabilitation apparatus that is attachable to a patient, musculoskeletal rehabilitation information about the patient;

automatically receiving, by a client-side application of a rehabilitation portal, the musculoskeletal rehabilitation information about the patient from the musculoskeletal rehabilitation apparatus via a short-range wireless connection, wherein the client-side application is operable on a mobile device;

processing, by the rehabilitation portal, the musculoskeletal rehabilitation information;

aggregating, by the rehabilitation portal, the musculoskeletal rehabilitation information; and generating, by the rehabilitation portal, one or more reports for one or more healthcare professionals based at least on the aggregated musculoskeletal rehabilitation information.

13. The method of claim 12, wherein:

the intelligent musculoskeletal rehabilitation apparatus includes one or more members that is attachable to the patient;

the one or more members includes a transmitter and at least one of an accelerometer, a sensor, or a memory; and the method further comprises gathering, by the musculoskeletal rehabilitation apparatus, the musculoskeletal rehabilitation information about the patient using the at least one of the accelerometer, the sensor, or the memory.

14. The method of claim 13, further comprising transmitting, by the transmitter, the musculoskeletal rehabilitation information to the rehabilitation portal.

15. The method of claim 13, further comprising:

storing, by the musculoskeletal rehabilitation apparatus, the gathered musculoskeletal rehabilitation information in the memory; and tracking individual progress of the patient based at least on the gathered musculoskeletal rehabilitation information.

16. The method of claim 12, wherein the musculoskeletal rehabilitation information is first musculoskeletal rehabilitation information, the method further comprising:

receiving, by the client-side application, second musculoskeletal rehabilitation information associated with the patient via a manual entry of the second musculoskeletal rehabilitation information using a touch-sensitive screen of the mobile device.

17. The method of claim 16, further comprising:
aggregating, by the client-side application of the rehabilitation portal, the first and second musculoskeletal rehabilitation information associated with the patient; and
causing the aggregated first and second musculoskeletal rehabilitation information to be transmitted, via a long-range cellular connection, to a server-side application operable on a remote server.

18. The method of claim 12, wherein:
the intelligent musculoskeletal rehabilitation apparatus includes a first member and a second member;
the first member includes a first sensor, and the second member includes a second sensor;
the first member is physically separate from the second member; and
the method further comprises:
    creating a logical pairing between the first member and the second member;
    indicating, by a paired indicator of the first member, whether or not the logical pairing between the first member and the second member has occurred;
    wrapping a first strap of the first member including the first sensor around a human limb that is proximately located to a human joint on one side thereof; and
    wrapping a second strap of the second member including the second sensor around the human limb that is proximately located to the human joint on another side thereof.

19. The method of claim 18, wherein the first member includes a first sensor, and the second member includes a second sensor, the method further comprising:
    wrapping a first strap of the first member including the first sensor around a human limb that is proximately located to a human joint on one side thereof, and
    wrapping a second strap of the second member including the second sensor around the human limb that is proximately located to the human joint on another side thereof.

20. The method of claim 12, wherein:
the musculoskeletal rehabilitation apparatus includes a first intelligent rehabilitation member and a second intelligent rehabilitation member;
the first intelligent rehabilitation member is attachable to the patient, and includes a first logic section, a first transmitter, a first accelerometer, a first sensor, and a first memory;
the second intelligent rehabilitation member is attachable to the patient, and includes a second logic section, a second transmitter, a second accelerometer, a second sensor, and a second memory;
the method further comprises:
    gathering, by the first logic section of the first intelligent rehabilitation member, a first portion of the musculoskeletal rehabilitation information about the patient using at least one of the first accelerometer, the first sensor, or the first memory;
    gathering, by the second logic section of the second intelligent rehabilitation member, a second portion of the musculoskeletal rehabilitation information about the patient using at least one of the second accelerometer, the second sensor, or the second memory;
    storing, by the first logic section, the first portion of the gathered musculoskeletal rehabilitation information in the first memory;
    storing, by the second logic section, the second portion of the gathered musculoskeletal rehabilitation information in the second memory;
    transmitting, by the first transmitter, the first portion of the musculoskeletal rehabilitation information to the second intelligent rehabilitation member;
    transmitting, by the second transmitter, the first portion and the second portion of the musculoskeletal rehabilitation information to the rehabilitation portal; and
    facilitating tracking, by the rehabilitation portal, of individual progress of the patient based at least on the transmitted first portion and the transmitted second portion of the musculoskeletal rehabilitation information.

* * * * *